(12) United States Patent
Sato (10) Patent No.: US 10,806,333 B2
(45) Date of Patent: Oct. 20, 2020

(54) THREE-DIMENSIONAL WIRING SUBSTRATE AND IMAGING UNIT

(71) Applicant: FUJIKURA LTD., Tokyo (JP)

(72) Inventor: Takao Sato, Sakura (JP)

(73) Assignee: Fujikura Ltd., Tokyo (JP)

( * ) Notice: Subject to any disclaimer, the term of this patent is extended or adjusted under 35 U.S.C. 154(b) by 0 days.

(21) Appl. No.: 16/390,217

(22) Filed: Apr. 22, 2019

(65) Prior Publication Data

US 2019/0343375 A1  Nov. 14, 2019

(30) Foreign Application Priority Data

May 9, 2018  (JP) .................................. 2018-090787

(51) Int. Cl.
  *A61B 1/05*  (2006.01)
  *H01L 27/148*  (2006.01)
(52) U.S. Cl.
  CPC ........ *A61B 1/051* (2013.01); *H01L 27/14806* (2013.01)
(58) Field of Classification Search
  CPC ................................................ H01L 27/14806
  USPC ........................................................ 174/261
  See application file for complete search history.

(56) References Cited

U.S. PATENT DOCUMENTS

| | | | |
|---|---|---|---|
| 2012/0104230 A1* | 5/2012 | Eismann ................ | A61B 1/051 |
| | | | 250/208.1 |
| 2017/0301433 A1* | 10/2017 | Sekido ..................... | H01R 9/05 |
| 2018/0006388 A1* | 1/2018 | Yamada ................... | H01R 9/05 |
| 2019/0216304 A1* | 7/2019 | Kimura ................. | G02B 23/24 |

FOREIGN PATENT DOCUMENTS

JP  2006-109097 A  4/2006

* cited by examiner

*Primary Examiner* — Stanley Tso
(74) *Attorney, Agent, or Firm* — Osha Liang LLP (57) ABSTRACT

A three-dimensional wiring substrate includes: a front plate having an electrode pad electrically connected to a solid-state image sensing device; a rear plate protruding toward a rear side of the front plate from an outer peripheral portion of a rear surface of the front plate; an internal conductor connection pad which is disposed on the rear surface and to which an internal conductor of a coaxial cable is electrically connected; an external conductor connection pad which is disposed on a connection-side main surface which is a surface on an opening angle side of the rear plate with respect to the rear surface and to which an external conductor of the coaxial cable is electrically connected; and an inter-pad connection wiring that secures at least one of electrical continuity of the internal conductor connection pad and electrical continuity of the external conductor connection pad.

7 Claims, 5 Drawing Sheets

THREE-DIMENSIONAL WIRING SUBSTRATE AND IMAGING UNIT

CROSS REFERENCE TO RELATED APPLICATIONS

This application claims priority from Japanese Patent Application No. 2018-090787 filed on May 9, 2018, the contents of which are incorporated herein by reference in their entirety.

TECHNICAL FIELD

The present invention relates to a three-dimensional wiring substrate electrically connected to a solid-state image sensing device such as a complementary metal oxide semiconductor (so-called CMOS), a charge coupled device (so-called CCD), or the like, and an imaging unit having a configuration in which a solid-state image sensing device is electrically connected to an electrical cable via a three-dimensional wiring substrate.

BACKGROUND

In an electronic endoscope, a configuration in which an imaging unit configured to electrically connect a solid-state image sensing device (hereinafter, also simply referred to as an imaging device) to a distal end of an electrical wire via a wiring substrate is housed in a flexible tube made of a resin is widely employed (for example, Japanese Unexamined Patent Application, First Publication No. 2006-109097).

In this type of imaging unit, distal ends of electrical wires are electrically connected to a plurality of wirings of the wiring substrate, and each electrical wire is electrically connected to the imaging device via a wiring of the wiring substrate.

The wiring substrate is disposed on a rear side of the imaging device by electrically connecting the wirings to electrodes on a rear surface of the imaging device opposite to an imaging surface at a front end thereof.

In imaging units used for endoscopes or the like, as a countermeasure against noise, use of coaxial cables for electrical wires has become common in recent years.

When a coaxial cable is used, a wiring substrate (coaxial cable wiring substrate) including an electrode pad (internal conductor connection pad) to which a distal end portion of an internal conductor of the coaxial cable is soldered, and an electrode pad (external conductor connection pad) to which a distal end portion of an external conductor of the coaxial cable is soldered is used. The coaxial cable wiring substrate includes a wiring for electrically connecting the internal conductor connection pad to the imaging device and a wiring for electrically connecting the external conductor connection pad to the imaging device.

A coaxial cable wiring substrate is roughly classified into a coaxial cable wiring substrate using a rigid substrate and a coaxial cable wiring substrate using a flexible printed wiring substrate (hereinafter also referred to as an FPC). The coaxial cable wiring substrate includes a connection front end portion connected to the imaging device by soldering the wiring of the coaxial cable wiring substrate to the electrode on the rear surface of the imaging device and a rear side extended portion extending toward a rear side of the imaging device from the connection front end portion. Generally, the rear side extended portion of the coaxial cable wiring substrate is in a flat plate shape or strip shape having a pair of the internal conductor connection pad and the external conductor connection pad on one side or both sides. The internal conductor connection pad and the external conductor connection pad are provided separately from each other in an extending direction (front-rear direction) of the rear side extended portion.

An imaging unit has a rigid portion that does not easily bend at a front end portion at which an imaging device is positioned.

For example, an imaging unit in which a rigid coaxial cable wiring substrate is used may include a rigid portion constituted by an imaging device, a lens unit fixed to a front end surface of the imaging device, a coaxial cable wiring substrate provided on a rear side of the imaging device, and soldered portions in which respective distal end portions of an internal conductor and an external conductor of a coaxial cable are soldered to electrode pads of the coaxial cable wiring substrate.

The soldered portions include solder that has soldered the respective distal end portions of the internal conductor and the external conductor of the coaxial cable to the electrode pads of the coaxial cable wiring substrate.

A rear side extended portion of a coaxial cable wiring substrate in a conventional structure using an FPC (hereinafter referred to as a coaxial cable FPC) has a certain level of flexibility before an internal conductor and an external conductor of the coaxial cable are soldered. However, in the rear side extended portion of the coaxial cable FPC, in a state in which the internal conductor and the external conductor of the coaxial cable are respectively soldered to an internal conductor connection pad and an external conductor connection pad, an entire region in which the coaxial cable is provided substantially becomes a part of a rigid portion due to rigidity of the coaxial cable provided along the rear side extended portion and rigidity of soldered portions of the internal conductor and the external conductor.

The imaging unit of the conventional structure assembled using the coaxial cable FPC includes a rigid portion constituted by an imaging device, a lens unit, a coaxial cable wiring substrate, and soldered portions in which the internal conductor and the external conductor of the coaxial cable are soldered with respect to electrode pads of the rear side extended portion of the coaxial cable wiring substrate.

In an imaging unit used for endoscopes or the like, when a length of the rigid portion of the front end portion at which the imaging device is positioned (a dimension in a front-rear direction of the imaging device, hereinafter, also referred to as a rigid portion length) is long, if a swinging operation for changing a direction of the front end portion of the imaging unit at which the imaging device is positioned is performed in a narrow conduit or the like, a case in which a movable range of the front end portion of the imaging unit due to a swinging operation cannot be sufficiently secured is likely to occur. Therefore, the length of the rigid portion of the front end portion (a dimension in a front-rear direction of the imaging device, also referred to as a rigid portion length) is required to be reduced in the imaging unit.

In view of this requirement, in the conventional coaxial cable wiring substrate, reducing an extended length of the rear side extended portion from the connection front end portion is being investigated. However, in the conventional coaxial cable wiring substrate, in order to prevent short-circuiting between the soldered portions of the internal conductor and the external conductor of the coaxial cable, it is necessary to secure a separation distance in an extending direction (front-rear direction) of the rear side extended portion between the internal conductor connection pad and the external conductor connection pad. Therefore, in the conventional imaging unit, it has been difficult to reduce an extension dimension of the rear side extended portion of the coaxial cable wiring substrate and reduce the rigid portion length.

SUMMARY

According to one or more embodiments of the invention, a three-dimensional wiring substrate and an imaging unit can easily realize reduction of a rigid portion length.

A three-dimensional wiring substrate according to one or more embodiments of the invention includes a front plate having an electrode pad electrically connected to a solid-state image sensing device formed on a front surface thereof, a rear plate protruding toward a rear side of the front plate from a part of an outer peripheral portion of a rear surface on a side opposite to the front surface of the front plate, an internal conductor connection pad which is formed on the rear surface of the front plate and to which an internal conductor of a coaxial cable is electrically connected, an external conductor connection pad which is formed on a connection-side main surface which is a surface on an opening angle side of the rear plate with respect to the rear surface of the front plate and to which an external conductor of the coaxial cable is electrically connected, and an inter-pad connection wiring configured to secure each of electrical continuity of the internal conductor connection pad and electrical continuity of the external conductor connection pad with the corresponding electrode pads.

In the three-dimensional wiring substrate according to one or more embodiments, an internal corner portion curved surface curved so that an inclination angle with respect to the rear surface of the front plate is decreased in a direction from the connection-side main surface toward the front plate may be formed between the rear surface of the front plate and the connection-side main surface of the rear plate.

The three-dimensional wiring substrate according to one or more embodiments may further include a rear plate partition wall formed to extend in a front-rear direction perpendicular to the front surface of the front plate at one or a plurality of positions in a width direction along a front end portion of the rear plate on the connection-side main surface of the rear plate, in which the external conductor connection pad may be formed in each of regions on both sides with the rear plate partition wall interposed therebetween in the width direction of the connection-side main surface, and the internal conductor connection pad may be formed at a plurality of positions corresponding to the external conductor connection pads in the width direction of the rear surface of the front plate.

The three-dimensional wiring substrate according to one or more embodiments may further include a front plate partition wall formed to extend in a front-rear direction perpendicular to the front surface of the front plate and in a vertical direction perpendicular to the width direction at one or a plurality of positions in a width direction along a front end portion of the rear plate on the rear surface of the front plate, in which the internal conductor connection pad may be formed in each of regions on both sides with the front plate partition wall interposed therebetween in the width direction of the rear surface of the front plate, and the external conductor connection pad may be formed at a plurality of positions corresponding to the internal conductor connection pads in the width direction of the connection-side main surface of the rear plate.

According to one or more embodiments, the rear plate may protrude obliquely with respect to the rear surface of the front plate from the front plate to a rear side with an opening angle of 90 to 135 degrees secured with respect to the rear surface.

An imaging unit according to one or more embodiments of the invention includes the above-described three-dimensional wiring substrate, the solid-state image sensing device electrically connected to an electrode pad on the front surface of the front plate of the three-dimensional wiring substrate, and the coaxial cable in which the internal conductor is electrically connected to the internal conductor connection pad of the three-dimensional wiring substrate and the external conductor is electrically connected to the external conductor connection pad of the three-dimensional wiring substrate, in which the coaxial cable includes an inner covered wire having a configuration in which the internal conductor is covered with an inner insulating layer provided between the internal conductor and the external conductor around the internal conductor, a distal end portion of the internal conductor protruding from a distal end of a front side extended portion of the inner covered wire exposed at a distal end of the coaxial cable is electrically connected to the internal conductor connection pad, and a curved portion curved so that an inclination angle with respect to the rear surface of the front plate is decreased in a direction toward the front plate is formed in the front side extended portion of the inner covered wire.

The imaging unit according to one or more embodiments may further include a lens unit fixed to a front surface of the solid-state image sensing device on a side opposite to a rear surface thereof to which an electrode pad on the front surface of the front plate of the three-dimensional wiring substrate is electrically connected.

According to one or more embodiments of the three-dimensional wiring substrate and the imaging unit, a dimension of the three-dimensional wiring substrate in a front-rear direction (a direction perpendicular to the front surface of the front plate) may be reduced to be small by a configuration in which the external conductor connection pad is formed on the connection-side main surface of the rear plate protruding to rearward from the front plate in which the internal conductor connection pad is formed. As a result, in the imaging unit, a dimension in the front-rear direction of the rigid portion (a rigid portion length) including the imaging device, the three-dimensional wiring substrate, and portions of the respective distal end portions of the internal conductor and the external conductor of the coaxial cable fixed to the electrode pads of the coaxial cable wiring substrate by soldering (a lens unit also is included when the lens unit is fixed to a front surface of the imaging device) may be reduced to be small, and a large movable range of the imaging device in a swinging operation may be secured compared to the case in which a coaxial cable wiring substrate with a conventional structure is used.

DETAILED DESCRIPTION

Hereinafter, a three-dimensional wiring substrate and an imaging unit according to embodiments of the invention will be described with reference to the drawings.

Figure 1:
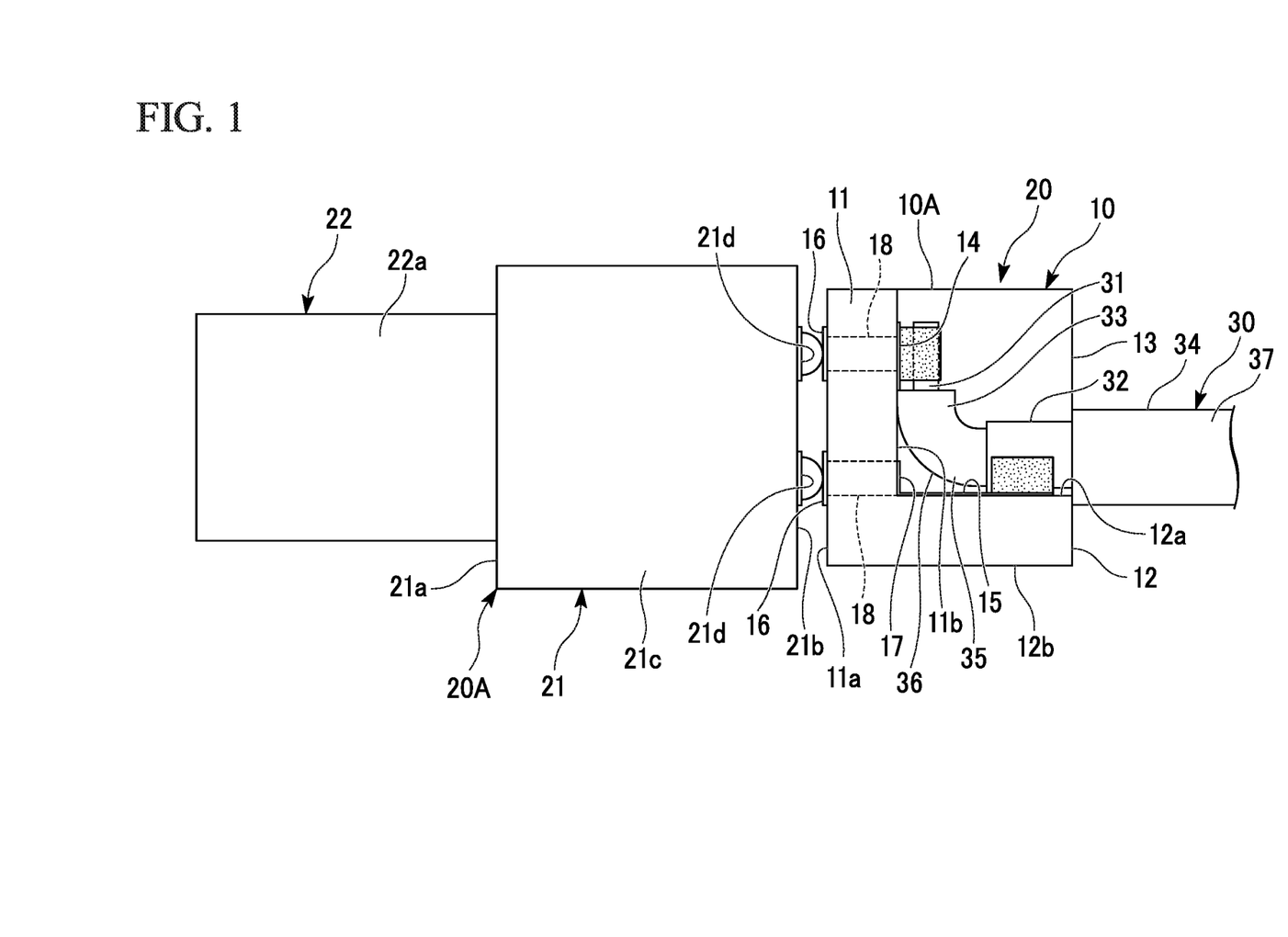
FIG. 1 is a front view showing an example of an imaging unit assembled using a three-dimensional wiring substrate according to one or more embodiments of the invention.
Figure 2:
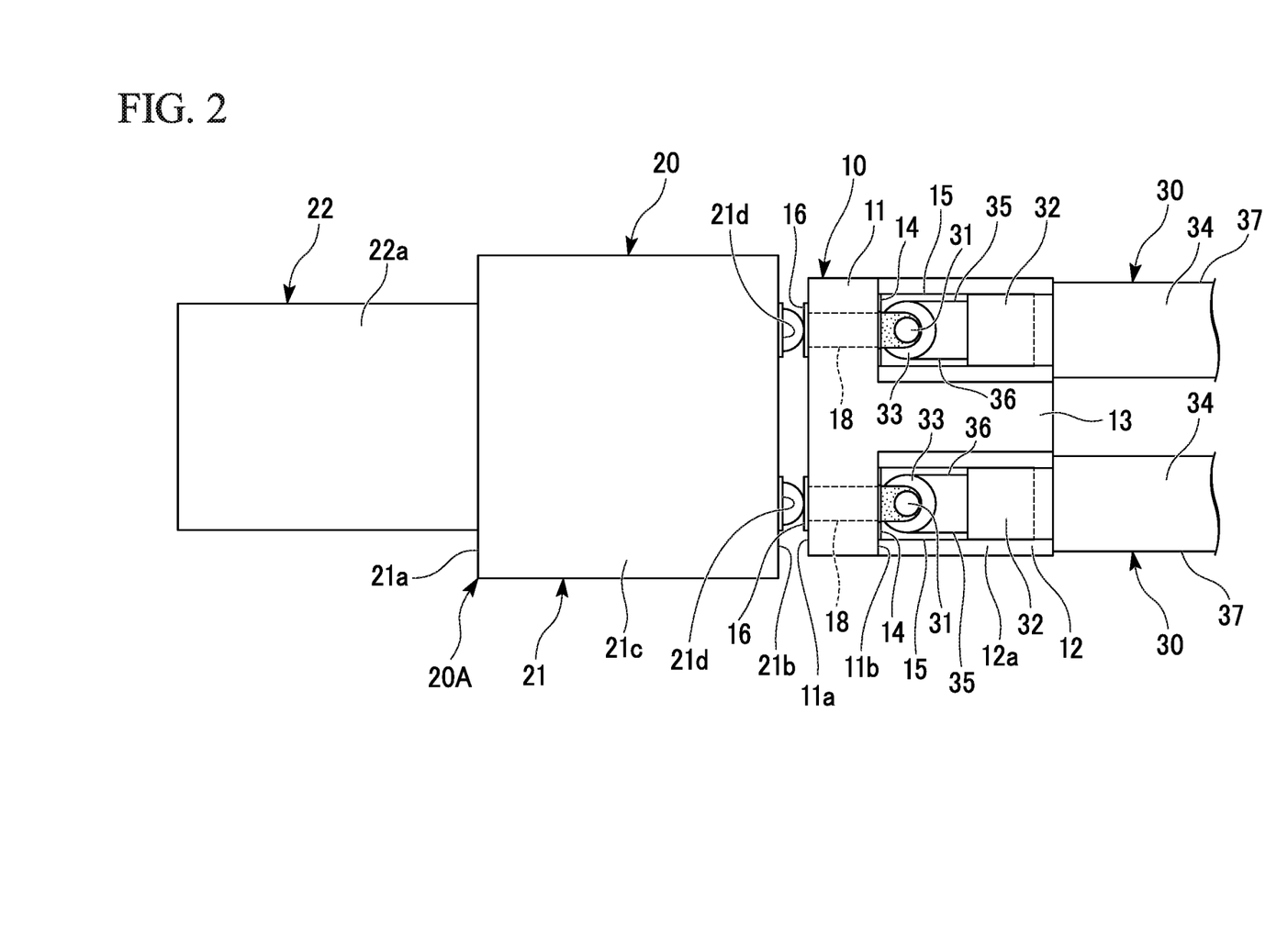
FIG. 2 is a plan view showing the imaging unit of FIG. 1.

FIGS. 1 and 2 show an example of an imaging unit 20 assembled using a three-dimensional wiring substrate 10 according to one or more embodiments of the invention.

FIGS. 1 and 2 are views showing a vicinity of the three-dimensional wiring substrate 10 of the imaging unit 20, in which FIG. 1 is a front view, and FIG. 2 is a plan view.

The imaging unit 20 shown in FIGS. 1 and 2 includes a solid-state image sensing device 21 (hereinafter also simply referred to as an imaging device), a lens unit 22 fixed to a front surface 21a of an imaging device 21, the three-dimensional wiring substrate 10 attached to a rear surface 21b on a side opposite to the front surface 21a of the imaging device 21, and a coaxial cable 30 electrically connected to electrode pads 14 and 15 of the three-dimensional wiring substrate 10.

A complementary metal oxide semiconductor (a so-called CMOS), a charge coupled device (a so-called CCD), or the like is used for the imaging device 21.

The imaging device 21 includes a device main body 21c having the rear surface 21b formed on a side opposite to the front surface 21a to be parallel to the front surface 21a, and an electrode pad 21d formed on the rear surface 21b of the device main body 21c.

The device main body 21c shown in FIGS. 1 and 2 is a member formed in a rectangular parallelepiped shape. However, a specific shape of the device main body 21c is not limited to a rectangular parallelepiped shape, and may be, for example, a columnar shape or the like.

The lens unit 22 has a configuration in which a lens is housed in a lens barrel 22a. The lens unit 22 is aligned with the front surface 21a of the imaging device 21 such that the lens in the lens barrel 22a is positioned on a light receiving optical axis of an imaging surface of the front surface 21a of the imaging device 21, and fixed to the imaging device 21.

The imaging device 21 receives light incident on the imaging surface from a front side of the lens unit 22 via an inner region of the lens barrel 22a to capture an image.

The imaging unit 20 includes an imaging head 20A constituted by the imaging device 21, the lens unit 22, and the three-dimensional wiring substrate 10.

Regarding the imaging head 20A, a front-rear direction of the imaging device 21 (a distance direction between the front surface 21a and the rear surface 21b) is referred to as a front-rear direction. Also, regarding the imaging head 20A, the lens unit 22 side is referred to as a front side, and the three-dimensional wiring substrate 10 side is referred to as a rear side.

Regarding the coaxial cable 30 of the imaging unit 20, the imaging head 20A side in a longitudinal direction of the coaxial cable 30 is referred to as a "front side," and a side opposite thereto is referred to as a "rear side."

The three-dimensional wiring substrate 10 includes a substrate main body 10A constituted by a front plate 11 disposed perpendicular to the front-rear direction of the imaging device 21 on the rear side of the imaging device 21 (rear surface 21b side), a rear plate 12 protruding rearward (toward a side opposite to the imaging device 21) from a part of an outer periphery of the front plate 11, and a partition wall 13.

Figure 3:
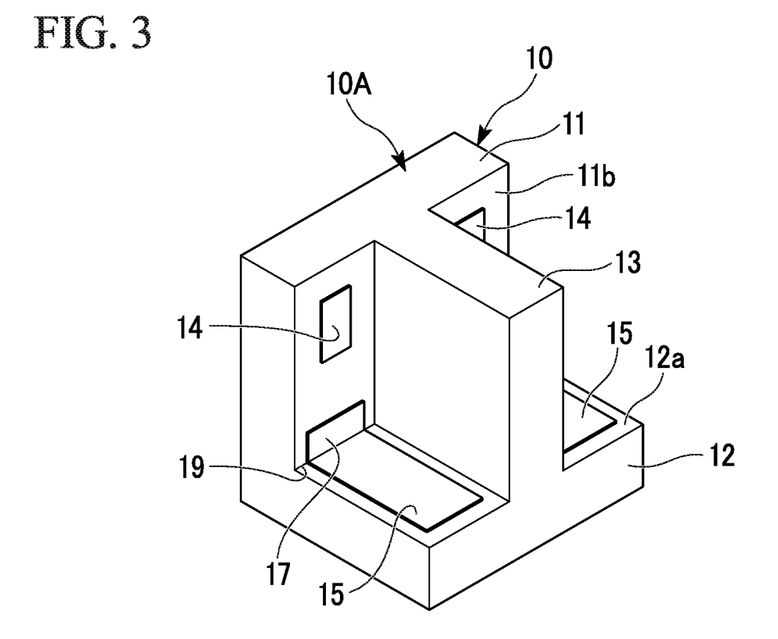
FIG. 3 is a perspective view showing a structure of the three-dimensional wiring substrate of an imaging head of the imaging unit of FIG. 1 when viewed obliquely from the rear.

The front plate 11 and the rear plate 12 of the three-dimensional wiring substrate 10 shown in FIGS. 1 to 3 are each in a rectangular plate shape. The rear plate 12 is formed to protrude from a region along one of four sides of an outer periphery of the front plate 11 in an outer peripheral portion of the front plate 11 toward the rear side of the front plate 11 in a direction perpendicular to the front plate 11.

A direction along a boundary portion (boundary line 19) of surfaces of the front plate 11 and the rear plate 12 of the three-dimensional wiring substrate 10 on an opening angle side (internal corner portion side) of each other is hereinafter referred to as a width direction.

The boundary portion (boundary line 19) of the surfaces of the front plate 11 and the rear plate 12 on the opening angle side (internal corner portion side) of each other extends along a front end portion which is an end portion of the rear plate 12 on the front plate 11 side.

The partition wall 13 is formed in a plate shape to extend rearward from the entire region of a central portion in the width direction of the front plate 11 up to a rear end portion of the rear plate 12 in a direction perpendicular to the front plate 11 and the rear plate 12. Also, the partition wall 13 is integrally formed with the front plate 11 and the rear plate 12.

The substrate main body 10A is formed of an electrically insulating material such as a resin.

A material for forming the substrate main body 10A is not limited to a resin, and may be, for example, ceramics or the like.

As shown in FIGS. 1 and 2, the three-dimensional wiring substrate 10 includes an electrode pad 16 (hereinafter also referred to as a device connection pad) formed on a front surface 11a of the front plate 11 facing the imaging device 21.

The imaging device 21 is attached to the three-dimensional wiring substrate 10 by soldering the electrode pad 21d provided on the rear surface 21b of the imaging device 21 to the device connection pad 16 of the three-dimensional wiring substrate 10.

The electrode pad 21d on the rear surface 21b of the imaging device 21 is soldered to the device connection pad 16 of the three-dimensional wiring substrate 10, for example, by heat-melting a solder bump provided on the electrode pad 21d and by cooling and solidifying thereafter.

However, the soldering between the electrode pad 21d on the rear surface 21b of the imaging device 21 and the device connection pad 16 of the three-dimensional wiring substrate 10 may be performed by solder separately supplied between the electrode pad 21d and the device connection pad 16 without using a solder bump.

FIG. 3 is a perspective view showing a structure of the three-dimensional wiring substrate 10 when viewed obliquely from the rear of the three-dimensional wiring substrate 10.

As shown in FIGS. 1 to 3, the three-dimensional wiring substrate 10 includes the electrode pad 14 (hereinafter also referred to as an internal conductor connection pad) formed on a rear surface 11b (hereinafter also referred to as a front plate rear surface) on a side opposite to the front surface 11a of the front plate 11, and the electrode pad 15 (hereinafter also referred to as an external conductor connection pad) formed on the rear plate 12 of the substrate main body 10A.

Specifically, the external conductor connection pad 15 is formed to extend on a connection-side main surface 12a of the rear plate 12 which is a surface on an opening angle side with respect to the rear surface 11b of the front plate 11 in the substrate main body 10A.

As shown in FIGS. 1 and 2, distal end portions of an internal conductor 31 and an external conductor 32 exposed at a distal end of the coaxial cable 30 are electrically connected to the electrode pads 14 and 15, respectively.

The distal end portion of the internal conductor 31 of the coaxial cable 30 is soldered to the internal conductor connection pad 14 of the three-dimensional wiring substrate 10. A distal end portion of the external conductor 32 of the coaxial cable 30 is soldered to the external conductor connection pad 15 of the three-dimensional wiring substrate 10.

The coaxial cable 30 includes the internal conductor 31, an inner insulating layer 33 covering a surrounding circumference of the internal conductor 31, the external conductor 32 provided to cover a surrounding circumference of the inner insulating layer 33, and an outer insulating layer 34 covering the external conductor 32. The coaxial cable 30 has flexibility.

The inner insulating layer 33 and the outer insulating layer 34 are formed of an electrically insulating resin material.

The outer insulating layer 34 serves the role of an outer coating forming a surrounding circumferential surface of the coaxial cable 30.

The internal conductor 31 is formed with one or a plurality of element wires.

The external conductor 32 is constituted by a plurality of element wires and is provided between the inner insulating layer 33 and the outer insulating layer 34.

Element wires forming the internal conductor 31 and element wires forming the external conductor 32 are formed of a highly conductive metal such as copper or the like.

An inner covered wire 35 having a configuration in which a surrounding circumference of the internal conductor 31 is covered with the inner insulating layer 33, and the distal end portion of the external conductor 32 are extended from a distal end of the outer insulating layer 34 of the coaxial cable 30.

An extended dimension of the inner covered wire 35 from the distal end of the outer insulating layer 34 is secured much larger than an extended dimension of the external conductor 32 from the distal end of the outer insulating layer 34.

The coaxial cable 30 is attached to the three-dimensional wiring substrate 10 by soldering the distal end portion of the internal conductor 31 to the internal conductor connection pad 14 of the three-dimensional wiring substrate 10 and soldering the distal end portion of the external conductor 32 to the external conductor connection pad 15 of the three-dimensional wiring substrate 10.

The distal end portion of the internal conductor 31 soldered to the internal conductor connection pad 14 of the three-dimensional wiring substrate 10 is a part of the internal conductor 31 extended from the distal end of the inner covered wire 35 (specifically, the inner insulating layer 33).

As shown in FIG. 1, in a portion of the inner covered wire 35 (front side extended portion) extended from the distal end of the outer insulating layer 34 of the coaxial cable 30, a curved portion 36 curved so that an inclination angle with respect to the connection-side main surface 12a of the three-dimensional wiring substrate 10 is increased in a direction from a rear end to a front end side thereof is formed.

The distal end portion of the external conductor 32 extended from the distal end of the outer insulating layer 34 of the coaxial cable 30 is disposed to extend along the connection-side main surface 12a of the substrate main body 10A. The distal end portion of the internal conductor 31 extended from the distal end of the inner covered wire 35 is disposed to extend along the rear surface 11b of the front plate 11 of the substrate main body 10A.

As shown in FIGS. 1 to 3, the external conductor connection pad 15 is formed to extend from a rear end portion of the connection-side main surface 12a (hereinafter also referred to as a rear plate connection-side main surface) of the rear plate 12 of the three-dimensional wiring substrate 10 throughout to a front end thereof.

The distal end portion of the external conductor 32 extended from the distal end of the outer insulating layer 34 of the coaxial cable 30 is soldered to the external conductor connection pad 15 at a position spaced rearward from the rear surface 11b of the front plate 11 of the three-dimensional wiring substrate 10.

In the front side extended portion of the inner covered wire 35 extended from the distal end of the outer insulating layer 34 of the coaxial cable 30, a portion curved so that an inclination angle with respect to the rear plate connection-side main surface 12a is increased in a direction toward the front plate 11 is a portion positioned on the front plate 11 side with respect to a portion at which the distal end portion of the external conductor 32 is fixed and integrated with the external conductor connection pad 15 by being soldered to the external conductor connection pad 15.

As shown in FIGS. 1 and 2, the three-dimensional wiring substrate 10 of the imaging unit 20 of one or more embodiments includes a plurality (two in FIGS. 1 and 2) of pairs of the internal conductor connection pad 14 and external conductor connection pad 15. Only one coaxial cable 30 is electrically connected to a pair of the internal conductor connection pad 14 and the external conductor connection pad 15. The external conductor 32 of the coaxial cable 30 is electrically connected to the external conductor connection pad 15 which forms a pair with the internal conductor connection pad 14 which is electrically connected to the internal conductor 31 of the coaxial cable 30.

The imaging unit 20 includes the same number of coaxial cables 30 as the number of pairs of the internal conductor connection pad 14 and the external conductor connection pad 15 of the three-dimensional wiring substrate 10. The imaging unit 20 includes a plurality (two in FIGS. 1 and 2) of coaxial cables 30 electrically connected to respective pairs of the electrode pads 14 and 15 of the three-dimensional wiring substrate 10.

In the three-dimensional wiring substrate 10 shown in FIGS. 1 and 2, one pair of the internal conductor connection pad 14 and the external conductor connection pad 15 are provided on each of the left and right sides with the partition wall 13 interposed therebetween.

When the distal end portions of the internal conductor 31 and the external conductor 32 of the coaxial cable 30 are respectively soldered to the internal conductor connection pad 14 and the external conductor connection pad 15, the partition wall 13 prevents short-circuiting between the internal conductor connection pads 14 adjacent to each other and between the external conductor connection pads 15 adjacent to each other in the width direction of the three-dimensional wiring substrate 10 due to solder spread from the internal conductor connection pad 14 and the external conductor connection pad 15.

Also, when the respective distal end portions of the internal conductor 31 and the external conductor 32 of the coaxial cable 30 are soldered to the internal conductor connection pad 14 and the external conductor connection pad 15, the partition wall 13 of the three-dimensional wiring substrate 10 shown in FIGS. 1 and 2 can be used for roughly positioning the distal end portion of the coaxial cable 30 with respect to the internal conductor connection pad 14 and the external conductor connection pad 15.

When the distal end portion of the coaxial cable 30, for example, is brought closer to the internal conductor connection pad 14 and the external conductor connection pad 15 along with the partition wall 13 of the three-dimensional wiring substrate 10, the distal end portions of the internal conductor 31 and the external conductor 32 can be simply and roughly positioned with respect to the internal conductor connection pad 14 and the external conductor connection pad 15.

Therefore, employment of the three-dimensional wiring substrate 10 having the partition wall 13 can improve workability in the operation of soldering the distal ends of the internal conductor 31 and the external conductor 32 of the coaxial cable 30 to the internal conductor connection pad 14 and the external conductor connection pad 15 of the three-dimensional wiring substrate 10.

The coaxial cable 30 can be bent by a worker with a finger.

Also, the internal conductor 31 and the external conductor 32 of the coaxial cable 30 can be plastically deformed.

The worker can plastically deform the coaxial cable 30 with a finger due to the presence of the internal conductor 31 and the external conductor 32.

When the respective distal end portions of the internal conductor 31 and the external conductor 32 are soldered to the internal conductor connection pad 14 and the external conductor connection pad 15, it is preferable to cause the coaxial cable 30 to move to and approach the three-dimensional wiring substrate 10 with the curved portion 36 formed at the front side extended portion of the inner covered wire 35 in advance and bring the respective distal end portions of the internal conductor 31 and the external conductor 32 closer to and into contact with the electrode pads 14 and 15 of the three-dimensional wiring substrate 10.

The shape of the partition wall of the three-dimensional wiring substrate is not limited to a plate shape that extends rearward from the entire region of the central portion in the width direction of the front plate 11 to the rear end of the rear plate 12 of the three-dimensional wiring substrate 10 and is integrally formed with the front plate 11 and the rear plate 12 like the partition wall 13 of the three-dimensional wiring substrate 10 shown in FIGS. 1 and 2.

The partition wall of the three-dimensional wiring substrate may be formed, for example, in a rib shape that protrudes from a central portion in the width direction of the rear surface 11b of the front plate 11 and a central portion in the width direction of the connection-side main surface 12a of the three-dimensional wiring substrate 10 and extends in an L shape along the rear surface 11b of the front plate 11 and the connection-side main surface 12a.

The partition wall 13 shown in FIGS. 1 to 3 and the rib-shaped partition wall extending in an L shape along the rear surface 11b of the front plate 11 and the connection-side main surface 12a have a configuration in which a front plate partition wall extending in a vertical direction (vertical direction in FIG. 1 and vertical direction in FIG. 3) perpendicular to the front-rear direction and the width direction at the central portion in the width direction of the rear surface 11b of the front plate 11 and a rear plate partition wall extending in the front-rear direction at the central portion in the width direction of the connection-side main surface 12a are integrally formed.

In the present specification, regarding a vertical direction of the three-dimensional wiring substrate 10 and the imaging head 20A of the imaging unit 20 (vertical direction in FIG. 1 and vertical direction in FIG. 3), a side on which the rear plate 12 of the three-dimensional wiring substrate 10 is positioned is referred to as a lower side, and a side opposite thereto is referred to as an upper side.

The rear plate connection-side main surface 12a of the three-dimensional wiring substrate 10 shown in FIGS. 1 to 3 extends perpendicular to the vertical direction.

As shown in FIGS. 1 and 3, a surface 12b (bottom-side main surface) on a side opposite to the rear plate connection-side main surface 12a of the rear plate 12 of the three-dimensional wiring substrate 10 extends in parallel to the rear plate connection-side main surface 12a. The bottom-side main surface 12b of the rear plate 12 is positioned at a lowermost portion of the three-dimensional wiring substrate 10.

Next, the three-dimensional wiring substrate 10 will be described in more detail.

As shown in FIGS. 1 and 3, the three-dimensional wiring substrate 10 also includes a through wiring connection pad 17 which is an electrode pad formed on the rear surface 11b of the front plate 11 of the substrate main body 10A to secure electrical continuity with the external conductor connection pad 15.

The through wiring connection pad 17 of the three-dimensional wiring substrate 10 is formed to be continuous from the external conductor connection pad 15 formed on the rear plate 12 of the substrate main body 10A and extend to the rear surface 11b of the front plate 11.

Only one through wiring connection pad 17 is formed for one external conductor connection pad 15.

As shown in FIGS. 1 and 2, the same number of device connection pads 16 as the total number of internal conductor connection pads 14 and external conductor connection pads 15 are provided on the front surface 11a of the front plate 11 (hereinafter also referred to as a front plate front surface) of the three-dimensional wiring substrate 10.

The internal conductor connection pad 14 and the external conductor connection pad 15 are electrically connected to the device connection pads 16 via through wirings 18 each formed to penetrate and extend in a thickness direction of the substrate main body 10A in the front plate 11 of the substrate main body 10A.

The device connection pad 16 is formed in direct contact with one end in an extending direction of the through wiring 18 and to secure electrical continuity with the through wiring 18.

The internal conductor connection pad 14 is formed in direct contact with the other end on a side opposite to the one end of the through wiring 18 to secure electrical continuity with the through wiring 18.

The external conductor connection pad 15 is electrically connected to the device connection pad 16 via the through wiring connection pad 17 and the through wiring 18.

The through wiring connection pad 17 is formed in direct contact with an end (the other end) of the through wiring 18 on a side opposite to the device connection pad 16 to secure electrical continuity with the through wiring 18. The through wiring connection pad 17 is electrically connected to the device connection pad 16 via the through wiring 18.

The through wiring 18 positioned between the internal conductor connection pad 14 and the device connection pad 16 serves the role of an inter-pad connection wiring for electrically connecting between the internal conductor connection pad 14 and the device connection pad 16.

On the other hand, electrical connection between the external conductor connection pad 15 and the device connection pad 16 is formed via an inter-pad connection wiring constituted by the through wiring 18 positioned between the through wiring connection pad 17 and the device connection pad 16, and the through wiring connection pad 17.

Only one device connection pad 16 is electrically connected to each of the internal conductor connection pad 14 and the external conductor connection pad 15 of the three-dimensional wiring substrate 10 via the inter-pad connection wire.

The three-dimensional wiring substrate 10 includes the inter-pad connection wiring.

In the imaging unit 20 of FIGS. 1 and 2, the internal conductor 31 of the coaxial cable 30 is electrically connected to the imaging device 21 via the internal conductor connection pad 14 and the inter-pad connection wiring of the three-dimensional wiring substrate 10.

The external conductor 32 of the coaxial cable 30 is electrically connected to the imaging device 21 via the external conductor connection pad 15 and the inter-pad connection wiring of the three-dimensional wiring substrate 10.

In the imaging unit 20 shown in FIGS. 1 and 2, the whole of the imaging head 20A functions as a rigid portion in which bending deformation does not easily occur.

A dimension in the front-rear direction of the imaging head 20A is hereinafter also referred to as a rigid portion dimension.

The three-dimensional wiring substrate 10 of the imaging unit 20 shown in FIGS. 1 and 2 has a configuration including the front plate 11 on which the internal conductor connection pad 14 is formed, and the rear plate 12 having the external conductor connection pad 15 formed thereon and protruding rearward from the front plate 11. Therefore, the imaging unit 20 can reduce a rigid portion length (a dimension in the front-rear direction of the imaging head 20A) compared to a coaxial cable wiring substrate with a conventional structure.

As shown in FIGS. 1 and 3, in the imaging head 20A of the imaging unit 20, the internal conductor connection pad 14 formed on the front plate 11 is at a position shifted in a vertical direction with respect to the external conductor connection pad 15. The internal conductor connection pad 14 is at a position spaced upward from the external conductor connection pad 15.

In the vertical direction of the three-dimensional wiring substrate 10, the internal conductor connection pad 14 is formed only at an end portion (upper end portion) of the rear surface 11b of the front plate 11 on a side opposite to the rear plate 12, and is positioned at a place spaced upward not only from the external conductor connection pad 15 but also from the through wiring connection pad 17 formed on the rear surface 11b of the front plate 11.

In the present specification, hereinafter, a soldered portion (including solder) in which the distal end portion of the internal conductor 31 of the coaxial cable 30 is soldered to the internal conductor connection pad 14 is also called an internal conductor soldered portion, and a soldered portion (including solder) in which the distal end portion of the external conductor 32 of the coaxial cable 30 is soldered to the external conductor connection pad 15 is also called an external conductor soldered portion.

The internal conductor soldered portion and the external conductor soldered portion may be formed to protrude to an outer side from outer peripheries of the respective electrode pads 14 and 15 of the three-dimensional wiring substrate 10 due to spreading of solder or the like in some cases.

In a case of a configuration in which the internal conductor connection pad 14 is formed together with the external conductor connection pad 15 on the rear plate connection-side main surface 12a of the three-dimensional wiring substrate 10 (pad-aggregate structure on the same surface), in consideration of the protrusion of the internal conductor soldered portion and the external conductor soldered portion from the respective outer peripheries of the electrode pads 14 and 15 to the outside, it is necessary to secure a separation distance of the internal conductor connection pad 14 from the external conductor connection pad 15 so that contacting and short-circuiting between the soldered portions can be avoided.

On the other hand, as shown in FIGS. 1 and 3, with a configuration in which the internal conductor connection pad 14 is formed on the rear surface 11b of the front plate 11 which is different from the rear plate 12 on which the external conductor connection pad 15 is formed, it is sufficient if a separation distance that can prevent the internal conductor connection pad 14 from contacting and short-circuiting the through wiring connection pad 17 or the external conductor connection pad 15 due to spreading of solder or the like in the internal conductor soldered portion is secured between the through wiring connection pad 17 and the external conductor connection pad 15, and the internal conductor connection pad 14.

The through wiring connection pad 17 of the three-dimensional wiring substrate 10 shown in FIGS. 1 and 3 is formed to extend from the entire front end of the external conductor connection pad 15 to the rear surface 11b of the front plate 11. Regarding the three-dimensional wiring substrate 10 shown in FIGS. 1 and 3, it is sufficient if a separation distance that can prevent the internal conductor connection pad 14 from contacting and short-circuiting the through wiring connection pad 17 due to spreading of solder or the like in the internal conductor soldered portion is secured between the internal conductor connection pad 14 and the through wiring connection pad 17.

The separation distance secured for the purpose of preventing short-circuiting between the internal conductor connection pad 14 and the through wiring connection pad 17 (separation distance in the vertical direction on the rear surface 11b of the front plate 11) in the three-dimensional wiring substrate 10 shown in FIGS. 1 and 3, can be smaller than a separation distance secured for the purpose of preventing short-circuiting between an internal conductor soldered portion and an external conductor soldered portion in a pad-aggregate structure on the same surface.

Therefore, in the three-dimensional wiring substrate 10, it is possible to reduce a dimension in the vertical direction of the front plate 11 required for securing a separation distance that can prevent the internal conductor connection pad 14 from contacting and short-circuiting the through wiring connection pad 17 due to spreading of solder or the like in the internal conductor soldered portion between the internal conductor connection pad 14 and the through wiring connection pad 17 in the three-dimensional wiring substrate 10.

In the imaging unit 20 shown in FIG. 1, the front plate 11 of the three-dimensional wiring substrate 10 is formed such that the entirety of the three-dimensional wiring substrate 10 is positioned within a projection range in a front-rear direction of the device main body 21c of the imaging device 21.

The through wiring connection pad 17 is formed only at the end portion (lower end portion) of the rear surface 11b of the front plate 11 on the rear plate 12 side in the vertical direction of the three-dimensional wiring substrate 10.

Between the internal conductor connection pad 14 formed only on the upper end portion of the rear surface 11b of the front plate 11 of the three-dimensional wiring substrate 10 and the through wiring connection pad 17, a separation distance (separation distance in the vertical direction on the rear surface 11b of the front plate 11) that can prevent the internal conductor connection pad 14 from contacting and short-circuiting the through wiring connection pad 17 due to spreading of solder or the like in the internal conductor soldered portion is secured.

The configuration in which the internal conductor connection pad 14 is formed on the front plate 11 which is different from the rear plate 12 on which the external conductor connection pad 15 is formed can make it possible to reduce a dimension in the front-rear direction of the rear plate 12 of the three-dimensional wiring substrate 10 compared to the coaxial cable wiring substrate with the conventional structure or the above-described pad-aggregate structure on the same surface, and thus reduction of the dimension in the front-rear direction of the imaging head 20A (rigid portion length) can be realized.

The imaging head 20A of the imaging unit 20 can easily realize the prevention of short-circuiting between the soldered portions (including solder) in which the distal end portions of the internal conductor 31 and the distal end portion of the external conductor 32 of the coaxial cable 30 are respectively soldered to the electrode pads 14 and 15 of the three-dimensional wiring substrate 10 and the reduction of the dimension in the front-rear direction (rigid portion length) compared to the coaxial cable wiring substrate with the conventional structure.

The imaging unit 20 shown in FIGS. 1 and 2 can be housed, for example, in a flexible protective tube and used as a part of an endoscope (electronic endoscope) or the like.

Regarding the coaxial cable 30 of the imaging unit 20 shown in FIGS. 1 and 2, the portion 37 in which the outer insulating layer 34 is present is hereinafter also referred to as a cable main body.

The distal end portion of the external conductor 32 and the front side extended portion of the inner covered wire 35 shown in FIGS. 1 and 2 extend from a front end of the cable main body 37.

In an electronic endoscope in which the imaging unit 20 housed in a flexible protective tube is used, a configuration in which a swinging mechanism for changing a direction of the imaging head 20A (swinging operation) with respect to the cable main body is separately housed in the protective tube can also be employed.

The swinging mechanism changes a direction of the imaging head 20A with respect to the cable main body 37 by bending a front end portion (hereinafter also referred to as a "swinging bending portion") of the cable main body 37 of the coaxial cable 30 which is a portion positioned on a rear side from the imaging head 20A together with the protective tube and rotating the imaging head 20A around the swinging bending portion of the cable main body 37 of the coaxial cable 30.

Since the imaging unit 20 includes the imaging head 20A in which the rigid portion length can be reduced compared to a case in which the coaxial cable wiring substrate with the conventional structure is used, the imaging unit 20 is advantageous in securing an increased movable range of the imaging head 20A when the swinging operation is performed compared to the imaging unit in which the coaxial cable wiring substrate with the conventional structure is used.

Also, in the imaging unit 20 shown in FIGS. 1 and 2, the three-dimensional wiring substrate 10 is formed such that the entirety of the three-dimensional wiring substrate 10 is positioned within a projection range in a front-rear direction of the device main body 21c of the imaging device 21. Therefore, as the protective tube for housing the imaging unit 20 in the electronic endoscope, a protective tube having a cross-sectional size that allows a hollow portion inside the protective tube to house the imaging device 21 may be used, and it is unnecessary to employ a protective tube having a larger cross-sectional size of a hollow portion for housing the three-dimensional wiring substrate 10.

In the imaging unit 20 shown in FIGS. 1 and 2, the rectangular plate-shaped front plate 11 of the three-dimensional wiring substrate 10 is attached to the imaging device 21 in a direction in which four sides of an outer periphery in a planar direction of the front plate 11 are parallel to four sides of an outer periphery of the rectangular rear surface 21b of the rectangular parallelepiped device main body 21c. The front plate 11 of the three-dimensional wiring substrate 10 is formed such that the entirety of the three-dimensional wiring substrate 10 is positioned within a projection range of the rear surface 21b of the device main body 21c in the front-rear direction of the imaging device 21.

The configuration in which the entirety of three-dimensional wiring substrate 10 is positioned within the projection range in the front-rear direction of the device main body 21c of the imaging device 21 is a suitable configuration in the three-dimensional wiring substrate of various embodiments according to the invention irrespective of a shape of imaging devices, for example, such as a case of using a columnar imaging device.

In the three-dimensional wiring substrate 10 of the imaging unit 20 shown in FIGS. 1 and 2, the partition wall 13 does not protrude rearward from the rear plate 12 and does not protrude upward from the front plate 11 in the vertical direction on a side opposite to the rear plate 12.

The configuration in which the partition wall 13 does not protrude rearward from the rear plate 12 is preferable in terms of reducing a dimension in the front-rear direction of the imaging head 20A (rigid portion length) to be small.

The configuration in which the partition wall 13 does not protrude upward from the front plate 11 in the vertical direction of the three-dimensional wiring substrate 10 is preferable in terms of avoiding an increase in cross-sectional size of the protective tube that houses the imaging unit 20.

The configuration in which the partition wall does not protrude rearward from the rear plate and the configuration in which the partition wall does not protrude upward from the front plate are suitable configurations in the three-dimensional wiring substrate of various embodiments according to the invention.

(Modified Examples of Three-Dimensional Wiring Substrate)

Figure 4:
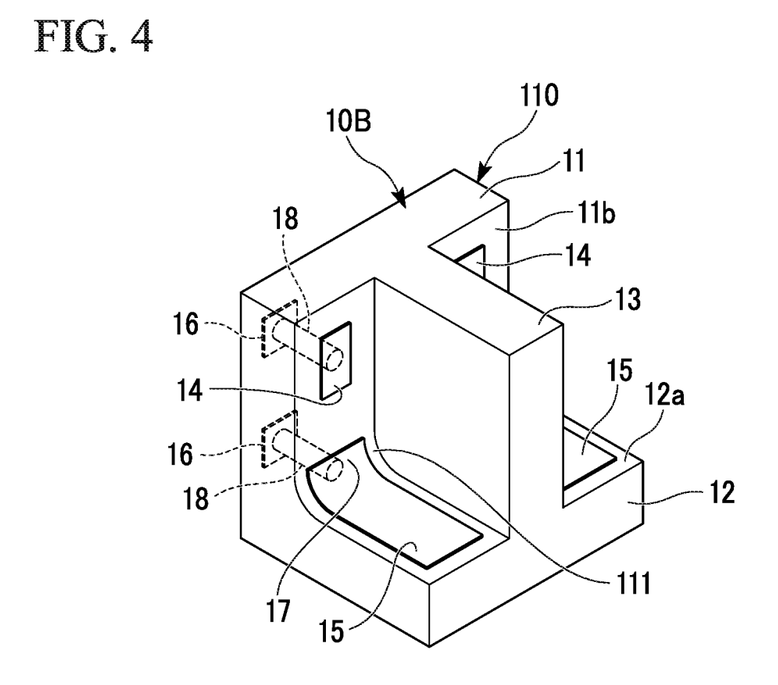
FIG. 4 is an explanatory view showing a first modified example of the three-dimensional wiring substrate and is a perspective view showing a structure of the three-dimensional wiring substrate when viewed obliquely from the rear.
Figure 5:
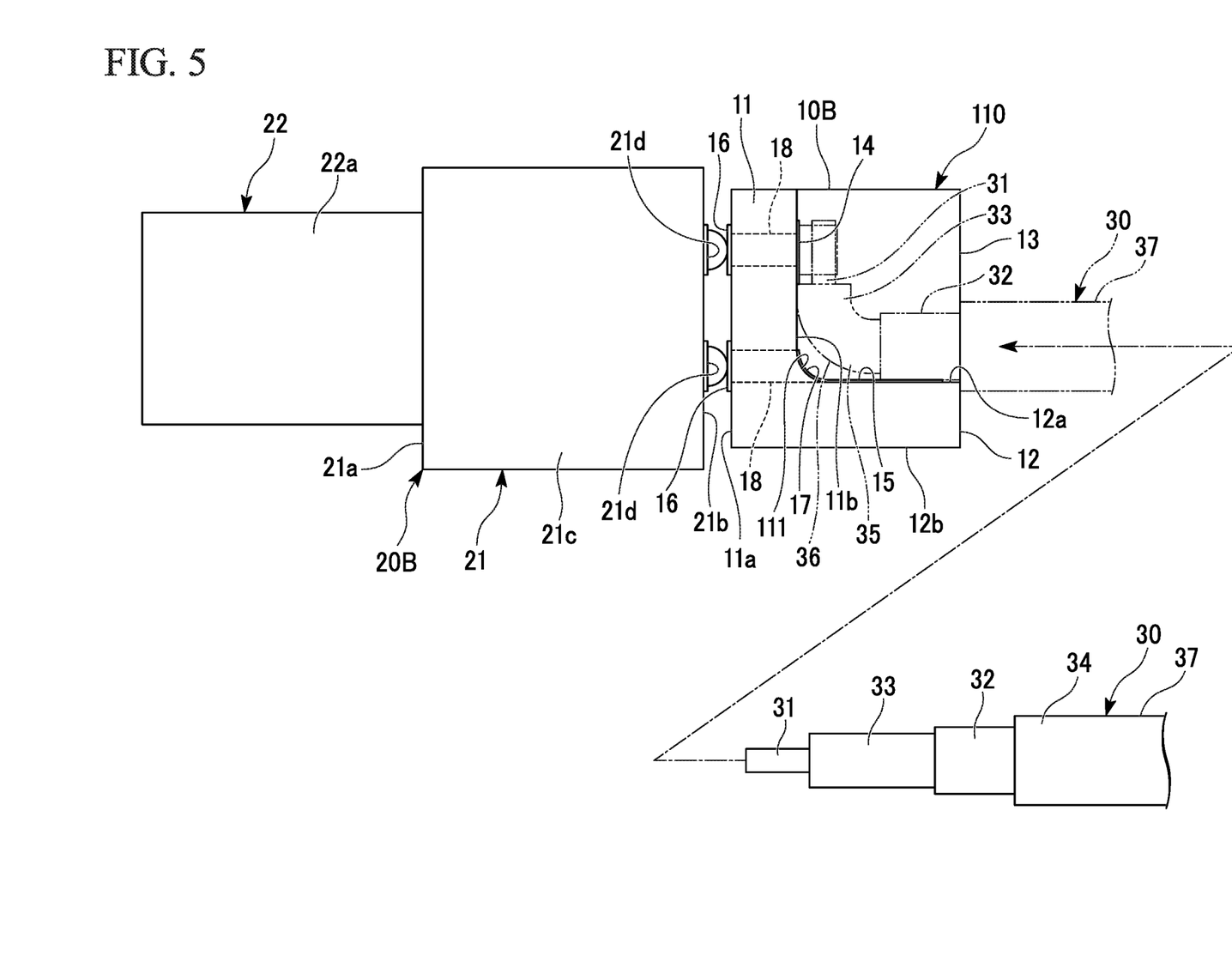
FIG. 5 is a front view showing an example of an imaging head assembled using the three-dimensional wiring substrate of FIG. 4.
Figure 6:
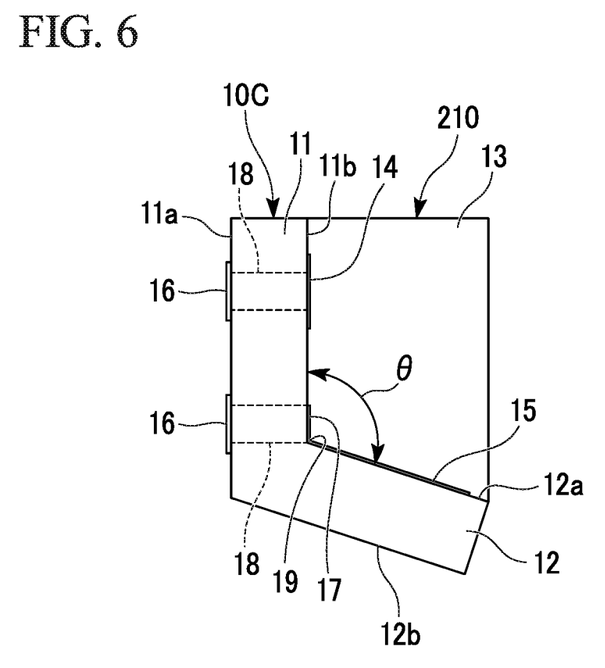
FIG. 6 is a front explanatory view showing a second modified example of the three-dimensional wiring substrate.

FIGS. 4 to 6 show modified examples of the three-dimensional wiring substrate.

The internal corner portion between the rear surface 11b of the front plate 11 and the rear plate connection-side main surface 12a of the three-dimensional wiring substrate 10 shown in FIGS. 1 to 3 is configured to have the boundary line 19 in which the rear surface 11b of the front plate 11 and the rear plate connection-side main surface 12a perpendicular to each other are in direct contact with each other.

A three-dimensional wiring substrate 110 (three-dimensional wiring substrate of a first modified example) shown in FIGS. 4 and 5 has a structure in which an internal corner portion curved surface 111 curved so that an inclination angle with respect to the rear plate connection-side main surface 12a is increased in a direction toward the front side is formed between the rear surface 11b of the front plate 11 of the substrate main body 10A and the rear plate connection-side main surface 12a of the three-dimensional wiring substrate 10 with respect to the three-dimensional wiring substrate 10 shown in FIGS. 1 to 3.

A reference numeral 10B in the drawing is added to a substrate main body of the three-dimensional wiring substrate 110 shown in FIGS. 4 and 5.

The substrate main body 10B of the three-dimensional wiring substrate 110 shown in FIGS. 4 and 5 differs from the substrate main body 10A of the three-dimensional wiring substrate 10 shown in FIGS. 1 to 3 only in terms of having the internal corner portion curved surface 111.

Configurations other than the internal corner portion curved surface 111 of the substrate main body 10B of the three-dimensional wiring substrate 110 shown in FIGS. 4 and 5 are the same as those of the substrate main body 10A of the three-dimensional wiring substrate 10 shown in FIGS. 1 to 3.

FIG. 5 shows an imaging head 20B having a configuration in which the three-dimensional wiring substrate 10 is changed to the three-dimensional wiring substrate 110 shown in FIG. 4 with respect to the imaging head 20A shown in FIGS. 1 and 2.

Further, in FIGS. 4 and 5, components similar to those in FIGS. 1 to 3 are denoted by the same reference numerals, and description thereof will be simplified or omitted.

In the three-dimensional wiring substrate 110 shown in FIGS. 4 and 5, a front end of the rear plate connection-side main surface 12a is a boundary with the internal corner portion curved surface 111, and a lower end in the vertical direction of the rear surface 11b of the front plate 11 (an end on the rear plate 12 side) is a boundary with the internal corner portion curved surface 111.

The internal corner portion curved surface 111 is formed to extend from a front end of the rear plate connection-side main surface 12a to a lower end of the rear surface 11b of the front plate 11.

In the three-dimensional wiring substrate 110 shown in FIGS. 4 and 5, the through wiring connection pad 17 is formed to be continuous from the external conductor connection pad 15. The through wiring connection pad 17 is formed to be curved along the internal corner portion curved surface 111. A surface of the through wiring connection pad 17 (surface on a side opposite to the internal corner portion curved surface 111) is curved along the internal corner portion curved surface 111.

The through wiring connection pad 17 is electrically connected to the device connection pad 16 on the front surface 11a of the front plate 11 through a through wiring formed to penetrate in a thickness direction of the front plate 11.

When distal end portions (front end portions) of the internal conductor 31 and the external conductor 32 of the coaxial cable 30 are respectively soldered to the electrode pads 14 and 15 of the three-dimensional wiring substrate 110 shown in FIG. 4, the coaxial cable 30 having a front end portion formed by exposing the distal end portion of the external conductor 32, a front side extended portion of the inner covered wire 35, and the distal end portion of the internal conductor 31 at a distal end (front end) of the cable main body 37 is prepared as shown in FIG. 5, and the front end portion of the coaxial cable 30 is caused to move forward toward the front plate 11 of the three-dimensional wiring substrate 110 while sliding the front side extended portion of the inner covered wire 35 on a surface of the external conductor connection pad 15 (a surface on a side opposite to the rear plate 12) of the three-dimensional wiring substrate 110.

As shown in FIG. 5, the front side extended portion of the inner covered wire 35 of the coaxial cable 30 is put in a state of extending in a straight line from the distal end of the cable main body 37 in the coaxial cable 30 before being brought into contact with the three-dimensional wiring substrate 110. Also, the distal end portion of the internal conductor 31 of the coaxial cable 30 is put in a state of extending in a straight line from a distal end of the front side extended portion of the inner covered wire 35 in the coaxial cable 30 before being brought into contact with the three-dimensional wiring substrate 110.

As the front end portion of the coaxial cable 30 moves forward in a direction toward the front plate 11 of the three-dimensional wiring substrate 110, the distal end portion of the internal conductor 31 of the coaxial cable 30 first approaches the internal conductor connection pad 14 while sliding on the surface of the through wiring connection pad 17 curved along the internal corner portion curved surface 111.

As the front end portion of the coaxial cable 30 moves forward in a direction toward the front plate 11 of the three-dimensional wiring substrate 110, the front side extended portion of the inner covered wire 35 of the coaxial cable 30 moves from the surface of the external conductor connection pad 15 to the surface of the through wiring connection pad 17, is deformed into a curved shape along the surface of the through wiring connection pad 17 while sliding on the surface of the through wiring connection pad 17 of the three-dimensional wiring substrate 110, and thereby the curved portion 36 is formed.

Accompanying the progressing of bending and deforming of the front side extended portion of the inner covered wire 35 along the surface of the through wiring connection pad 17, the distal end portion of the internal conductor 31 of the coaxial cable 30 changes its direction so that an inclination angle with respect to the rear surface 11b of the front plate 11 of the three-dimensional wiring substrate 110 is decreased and is brought into contact with a surface of the internal conductor connection pad 14 (surface on a side opposite to the front plate 11) of the three-dimensional wiring substrate 110 as the front end portion of the coaxial cable 30 moves forward in a direction toward the front plate 11 of the three-dimensional wiring substrate 110.

By adjusting an extended length of the front side extended portion of the inner covered wire 35 from the cable main body 37 and lengths of the respective distal end portions of the internal conductor 31 and the external conductor 32, the coaxial cable 30 is configured to realize contact of a surrounding circumferential surface of the distal end portion of the internal conductor 31 with respect to the surface of the internal conductor connection pad 14 and contact of a surrounding circumferential surface of the distal end portion of the external conductor 32 with respect to the surface of the external conductor connection pad 15.

By simply causing the coaxial cable 30 to move forward in a direction toward the front plate 11 along the surface of the external conductor connection pad 15 of the three-dimensional wiring substrate 110, formation of the curved portion 36 at the front side extended portion of the inner covered wire 35, contact of the distal end portion of the internal conductor 31 with the surface of the internal conductor connection pad 14, and contact of the distal end portion of the external conductor 32 with the surface of the external conductor connection pad 15 can be realized.

After realizing the formation of the curved portion 36 at the front side extended portion of the inner covered wire 35, the contact of the distal end portion of the internal conductor 31 with the surface of the internal conductor connection pad 14, and the contact of the distal end portion of the external conductor 32 with the surface of the external conductor connection pad 15, the coaxial cable 30 is attached to the three-dimensional wiring substrate 110 by soldering the distal end portion of the internal conductor 31 to the internal conductor connection pad 14 and soldering the distal end portion of the external conductor 32 to the external conductor connection pad 15.

When soldering of the distal end portion of the internal conductor 31 to the internal conductor connection pad 14 and soldering of the distal end portion of the external conductor 32 to the external conductor connection pad 15 are performed and thereby attachment of the coaxial cable 30 to the three-dimensional wiring substrate 110 of the imaging head 20B is completed, the imaging unit is obtained.

As shown in FIG. 6, a configuration employing a substrate main body 10C in which the opening angle θ between the rear surface 11b of the front plate 11 and the rear plate connection-side main surface 12a is greater than 90 degrees and equal to or less than 135 degrees can also be employed for the three-dimensional wiring substrate.

A three-dimensional wiring substrate 210 (three-dimensional wiring substrate of a second modified example) shown in FIG. 6 can be used as a part of the imaging head and the imaging unit.

Compared to the case in which the opening angle θ between the rear surface 11b of the front plate 11 and the rear plate connection-side main surface 12a is 90 degrees, the three-dimensional wiring substrate 210 shown in FIG. 6 can secure a wide space between the rear surface 11b of the front plate 11 and the rear plate connection-side main surface 12a. Therefore, compared to the case in which the opening angle θ between the rear surface 11b of the front plate 11 and the rear plate connection-side main surface 12a is 90 degrees, the three-dimensional wiring substrate 210 shown in FIG. 6 can improve workability in operations such as an operation of soldering the distal end portion of the internal conductor 31 of the coaxial cable 30 to the internal conductor connection pad 14, and an operation of soldering the distal end portion of the external conductor 32 of the coaxial cable 30 to the external conductor connection pad 15.

Further, the front surface 11a and the rear surface 11b of the front plate 11 of the three-dimensional wiring substrate 210 in FIG. 6 are parallel to each other as in the three-dimensional wiring substrate 10 shown in FIGS. 1 to 3.

Also, similarly to the three-dimensional wiring substrate 10 shown in FIGS. 1 to 3, the three-dimensional wiring substrate 210 shown in FIG. 6 is attached to the imaging device 21 by soldering the device connection pad 16 of the front surface 11a of the front plate 11 to the electrode pad 21d of the imaging device 21. Similar to the three-dimensional wiring substrate 10 shown in FIGS. 1 to 3, the three-dimensional wiring substrate 210 shown in FIG. 6 is attached to the imaging device 21 with the front surface 11a and the rear surface 11b of the front plate 11 being perpendicular to the front-rear direction of the imaging device 21.

When the three-dimensional wiring substrate 210 is attached to the imaging device 21, the rear plate connection-side main surface 12a of the three-dimensional wiring substrate 210 of FIG. 6 extends obliquely in the front-rear direction of the imaging device 21.

The three-dimensional wiring substrate can also employ a configuration in which the internal corner portion curved surface 111 is formed between the rear surface 11b of the front plate 11 and the rear plate connection-side main surface 12a of the three-dimensional wiring substrate 210 of FIG. 6.

While the invention has been described on the basis of one or more embodiments, the disclosure is not limited to the embodiments described above, and various modifications can be made without departing from the gist of the disclosure.

The inter-pad connection wiring for securing electrical continuity between the internal conductor connection pad 14 and the device connection pad 16 of the three-dimensional wiring substrate, and the inter-pad connection wiring for securing electrical continuity between the external conductor connection pad 15 and the device connection pad 16 are not limited to the configuration of including the through wiring 18, and may be a metal wiring or the like formed on an outer surface of the three-dimensional wiring substrate, for example. However, from a viewpoint of miniaturization of the three-dimensional wiring substrate, the configuration of the inter-pad connection wiring including the through wiring 18 is more advantageous compared to the metal wiring formed on an outer surface of the three-dimensional wiring substrate.

In addition to the configuration having the partition wall formed to be continuous from the connection-side main surface 12a to the rear surface 11b of the front plate 11, the three-dimensional wiring substrate can also employ a configuration in which a front plate partition wall formed to extend in the vertical direction at the central portion in the width direction of the rear surface 11b of the front plate 11 and a rear plate partition wall formed to extend in the front-rear direction at the central portion in the width direction of the connection-side main surface 12a are formed to be spaced apart from each other. The front plate partition wall and the rear plate partition wall formed to be spaced apart from each other are provided to form a pair (hereinafter also referred to as a partition wall pair) in which positions thereof in the width direction of the three-dimensional wiring substrate correspond to each other.

The pair of the front plate partition wall and the rear plate partition wall may be provided at a plurality of positions in the width direction of the three-dimensional wiring substrate.

However, each of the pair of the front plate partition wall and the rear plate partition wall is provided to be positioned between the pair of the internal conductor connection pad 14 and the external conductor connection pad 15 in the width direction of the three-dimensional wiring substrate.

The three-dimensional wiring substrate can also employ a configuration having only one of the front plate partition wall and the rear plate partition wall.

The front plate partition wall is provided between the internal conductor connection pads 14 adjacent to each other in the width direction of the three-dimensional wiring substrate.

The rear plate partition wall is provided between the external conductor connection pads 15 adjacent to each other in the width direction of the three-dimensional wiring substrate.

The external conductor 32 of the coaxial cable 30 is thicker than that of the internal conductor 31, and an amount of solder required for soldering the external conductor 32 to the electrode pad of the three-dimensional wiring substrate is also larger than that of the internal conductor 31.

The rear plate partition wall effectively contributes to the prevention of contact and short-circuiting between the external conductor soldered portions adjacent to each other in the width direction of the three-dimensional wiring substrate due to spreading of solder or the like of the external conductor soldered portion in which the external conductor 32 of the coaxial cable 30 is soldered to the external conductor connection pad 15.

The three-dimensional wiring substrate can also employ a configuration in which neither the partition wall, the front plate partition wall, nor the rear plate partition wall is present.

Electrical connection of the distal end portion of the internal conductor 31 of the coaxial cable 30 to the internal conductor connection pad 14 and electrical connection of the distal end portion of the external conductor 32 to the external conductor connection pad 15 are not limited to soldering, and, for example, thermal fusion such as laser processing, or the like also may be employed.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

What is claimed is:

1. A single-piece three-dimensional wiring substrate comprising:
    a front plate comprising an electrode pad electrically connected to a solid-state image sensing device disposed on a front surface of the front plate;
    a rear plate that is integrally formed with the front plate and that protrudes toward a rear side of the front plate from a part of an outer peripheral portion of a rear surface on a side opposite to the front surface of the front plate;
    an internal conductor connection pad disposed on the rear surface of the front plate and to which an internal conductor of a coaxial cable is electrically connected;
    an external conductor connection pad disposed on a connection-side main surface on an opening angle side of the rear plate with respect to the rear surface of the front plate and to which an external conductor of the coaxial cable is electrically connected; and
    an inter-pad connection wiring that secures at least one of electrical continuity of the internal conductor connection pad and electrical continuity of the external conductor connection pad with corresponding electrode pads, wherein
    a portion of the internal conductor extends along the connection side main surface of the rear plate and the rear surface of the front plate when the internal conductor is electrically connected to the internal conductor connection pad and the external conductor is electrically connected to the external conductor connection pad, and
    an internal corner portion curved surface is disposed between the rear surface of the front plate and the connection-side main surface of the rear plate,
    and the internal corner portion curved surface is curved so that an inclination angle with respect to the rear surface of the front plate decreases in a direction from the connection-side main surface toward the front plate.

2. The single-piece three-dimensional wiring substrate according to claim 1, further comprising:
    a rear plate partition wall extending in a front-rear direction perpendicular to the front surface of the front plate at one or more positions in a width direction along a front end portion of the rear plate on the connection-side main surface of the rear plate, wherein
    the external conductor connection pad is disposed on one side of the rear plate partition wall, and
    the internal conductor connection pad is disposed at a position corresponding to the external conductor connection pad in the width direction of the rear surface of the front plate.

3. The single-piece three-dimensional wiring substrate according to claim 1, further comprising:
    a front plate partition wall extending in a front-rear direction perpendicular to the front surface of the front plate and in a vertical direction perpendicular to the width direction at one or more positions in a width direction along a front end portion of the rear plate on the rear surface of the front plate, wherein
    the internal conductor connection pad is disposed on one side of the front plate partition wall, and
    the external conductor connection pad is disposed at a position corresponding to the internal conductor connection pad in the width direction of the connection-side main surface of the rear plate.

4. The single-piece three-dimensional wiring substrate according to claim 1, wherein
    the rear plate protrudes with respect to the rear surface of the front plate from the front plate rearward with an opening angle of 90 to 135 degrees secured with respect to the rear surface.

5. An imaging unit comprising:
    the single-piece three-dimensional wiring substrate according to claim 1;
    the solid-state image sensing device electrically connected to an electrode pad on the front surface of the front plate of the single-piece three-dimensional wiring substrate; and
    the coaxial cable, wherein
    the coaxial cable comprises an inner covered wire,
    the internal conductor is covered with an inner insulating layer provided between the internal conductor and the external conductor around the internal conductor,
    a distal end portion of the internal conductor protruding from a distal end of a front side extended portion of the inner covered wire exposed at a distal end of the coaxial cable is electrically connected to the internal conductor connection pad, and
    a curved portion that is curved so that an inclination angle with respect to the rear surface of the front plate is decreased in a direction toward the front plate is formed in the front side extended portion of the inner covered wire.

6. The imaging unit according to claim 5, further comprising a lens unit fixed to a front surface of the solid-state image sensing device on a side opposite to a rear surface of the solid-state image sensing device to which an electrode pad on the front surface of the front plate of the single-piece three-dimensional wiring substrate is electrically connected.

7. The single-piece three-dimensional wiring substrate according to claim 1, wherein the rear surface of the front plate with the internal conductor connection pad is perpendicular to the connection-side main surface of the rear plate with the external conductor connection pad.

* * * * *